(12) United States Patent
Boernert et al.

(10) Patent No.: US 10,591,562 B2
(45) Date of Patent: Mar. 17, 2020

(54) BONE MRI USING B0 INHOMOGENEITY MAP AND A SUBJECT MAGNETIC SUSCEPTIBILITY MAP

(71) Applicant: KONINKLIJKE PHILIPS N.V., Eindhoven (NL)

(72) Inventors: Peter Boernert, Eindhoven (NL); Kay Nehrke, Eindhoven (NL); Holger Eggers, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 250 days.

(21) Appl. No.: 15/735,314

(22) PCT Filed: Jun. 7, 2016

(86) PCT No.: PCT/EP2016/062820
§ 371 (c)(1),
(2) Date: Dec. 11, 2017

(87) PCT Pub. No.: WO2016/198363
PCT Pub. Date: Dec. 15, 2016

(65) Prior Publication Data
US 2018/0180693 A1 Jun. 28, 2018

(30) Foreign Application Priority Data
Jun. 12, 2015 (EP) .................................. 15171882

(51) Int. Cl.
*G01R 33/00* (2006.01)
*G01R 33/48* (2006.01)
(Continued)

(52) U.S. Cl.
CPC .......... *G01R 33/4816* (2013.01); *A61B 5/055* (2013.01); *A61N 5/1039* (2013.01);
(Continued)

(58) Field of Classification Search
CPC .............. G01R 33/4815; G01R 33/443; G01R 33/4812
See application file for complete search history.

(56) References Cited

U.S. PATENT DOCUMENTS 5,351,006 A 9/1994 Sumanaweera et al.
7,920,730 B2 4/2011 Jerebko
(Continued)

FOREIGN PATENT DOCUMENTS

| CN | 104267361 A | 1/2015 |
| RU | 2141256 C1 | 11/1999 |
| RU | 2511400 C1 | 4/2014 |

OTHER PUBLICATIONS

Koch et al, "Rapid Calculations of Susceptibility-Induced Magnetostatic Field Perturbations for In Vivo Magnetic Resonance", Phys. Med. Biol. 51 (2006) p. 6381-6402.
(Continued)

*Primary Examiner* — Joseph M Santos Rodriguez

(57) ABSTRACT

The invention provides for a medical instrument (100, 500) comprising a magnetic resonance imaging system (102) for acquiring magnetic resonance data (142) from a subject (118) within an imaging zone (108). The magnetic resonance imaging system comprises: a main magnet (104) for generating a B0 magnetic field within the imaging zone; a memory (134, 136) containing machine executable instructions (160, 162, 164, 166) and pulse sequence commands (140); a processor (130) for controlling the medical instrument. Execution of the machine executable instructions causes the processor to: acquire (200) the magnetic resonance data by controlling the magnetic resonance imaging system with the pulse sequence commands; receive (202) a subject magnetic susceptibility map (144) of the subject; calculate (204) a B0 inhomogeneity map (146) from the magnetic resonance data; calculate (206) a subject B0 mag-
(Continued)

netic field perturbation (148) from the subject magnetic susceptibility map; calculate (208) a residual B0 magnetic field perturbation (150) by subtracting the subject B0 magnetic field perturbation from the B0 inhomogeneity map; and calculate (210) a bone map (152) from the residual B0 magnetic field perturbation.

14 Claims, 6 Drawing Sheets

(51) Int. Cl.

| | | |
|---|---|---|
| *G01R 33/44* | (2006.01) | |
| *G01R 33/565* | (2006.01) | |
| *A61B 5/055* | (2006.01) | |
| *G01R 33/56* | (2006.01) | |
| *A61N 5/10* | (2006.01) | |

(52) U.S. Cl.
CPC ......... *A61N 5/1049* (2013.01); *G01R 33/443* (2013.01); *G01R 33/4812* (2013.01); *G01R 33/4828* (2013.01); *G01R 33/56* (2013.01); *G01R 33/56536* (2013.01); *G01R 33/56563* (2013.01); *A61N 2005/1055* (2013.01); *G01R 33/481* (2013.01)

(56) References Cited

U.S. PATENT DOCUMENTS

| | | | |
|---|---|---|---|
| 9,153,012 B2 | 10/2015 | Bredno | |
| 9,488,709 B2 | 11/2016 | Den Harder | |
| 9,659,370 B2 * | 5/2017 | Buerger | G01R 33/481 |
| 10,215,821 B2 * | 2/2019 | Yablonskiy | G01R 33/246 |
| 10,436,858 B2 * | 10/2019 | Shanbhag | |
| 2007/0081713 A1 | 4/2007 | Jerebko | |
| 2010/0142785 A1 | 6/2010 | Dahnke | |
| 2012/0277571 A1 | 1/2012 | Cho | |
| 2013/0266198 A1 | 10/2013 | Pereira et al. | |
| 2015/0145514 A1 | 5/2015 | Sharma et al. | |
| 2016/0054416 A1 | 2/2016 | Stehning et al. | |
| 2016/0169994 A1 | 6/2016 | Hu et al. | |

OTHER PUBLICATIONS

Tyler et al "Magnetic Resonance Imaging With Ultrashort TE (UTE) Pulse Sequences . . . " Journal of Magnetic Resonance Imaging 25.2 (2007) p. 279-289.

Bernstein et al "Handbook of MRI Pulse Sequences" Elsevier Academic Press, p. 857-887 (2004).

Jenkinson M et al: "Perturbation method for magnetic field calculations of nonconductive objects", Magnetic Resonance in Medicine, John Wiley & Sdns, Inc, US, vol. 52, No. 3, Sep. 1, 2004 (Sep. 1, 2004), pp. 471-477.

Yablonskiy D A: "Quantitation of intrinsic magnetic susceptibility-related effects in a tissue matrix. Phantom study",Magnetic Resonance in Medicine, John Wiley & Sons, Inc, US,vol. 39, No. 3, Mar. 1, 1998 (Mar. 1, 1998),pp. 417-428.

Strolka I et al: "Numerical simulation of trabecular bone magnetic resonance imaging".Proceedings of the 26th Annual International Conference of the IEEE EMBS San Francisco,CA, EMBS San Francisco, CA,USA,vol. 3, Sep. 1, 2004 (Sep. 1, 2004),p. 1088.

Moerland MA et al: "Analysis and Correction of Geometric Distortions in 1.5 T Magnetic Resonance Images for Use in Radiotherapy Treatment Planning", Physics in Medicine and Biology, Institute of Physics Publishing, Bristol GB, vol. 40, No. 10,Oct. 1, 1995 (Oct. 1, 1995), pp. 1651-1664.

Ericsson A ft al: "Measurements of Magnetic Field Variations in the Human Brain Using a 3D-FT Multiple Gradient Echo Technique",Magnetic Resonance in Medicine, John Wiley & Sons, Inc, US,vol. 33, No. 2,Feb. 1, 1995 (Feb. 1, 1995), pp. 171-177.

Glover G H: "Multipoint Dixon Technique for Water and Fat Proton and Susceptibility Imaging", Journal of Magnetic Resonance Imaging, Society for Magnetic Resonance Imaging, Oak Brook, IL, US, vol. 1, Jan. 1, 1991 (Jan. 1, 1991), pp. 521-530.

Sumanaweera T S et al: "MR Susceptibility Misregistration Correction", IEEE Transactions on Medical Imaging, IEEE Service Center, Piscataway, NJ, US, vol. 12, No. 2, Jun. 1, 1993 (Jun. 1, 1993), pp. 251-259.

* cited by examiner

BONE MRI USING B0 INHOMOGENEITY MAP AND A SUBJECT MAGNETIC SUSCEPTIBILITY MAP

CROSS REFERENCE TO RELATED APPLICATIONS

This application is a U.S. national phase application of International Application No. PCT/EP2016/062820, filed on Jun. 7, 2016, which claims the benefit of EP Application Serial No. 15171882.2 filed on Jun. 12, 2015 and is incorporated herein by reference.

TECHNICAL FIELD OF THE INVENTION

The invention relates to magnetic resonance imaging, in particular to the localization of bone tissue using perturbations of the B0 magnetic field.

BACKGROUND OF THE INVENTION

A large static magnetic field is used by Magnetic Resonance Imaging (MRI) scanners to align the nuclear spins of atoms as part of the procedure for producing images within the body of a patient. This large static magnetic field is referred to as the B0 field.

During an MRI scan, Radio Frequency (RF) pulses generated by one or more transmitter coils cause a called B1 field. Additionally applied gradient fields and the B1 field cause perturbations to the effective local magnetic field. RF signals are then emitted by the nuclear spins are detected by one or more receiver coils. These RF signals are used to construct the MR images. These coils can also be referred to as antennas. Further, the transmitter and receiver coils can also be integrated into one or more transceiver coils that perform both functions. It is understood that the use of the term transceiver coil also refers to systems where separate transmitter and receiver coils are used.

MRI scanners are able to construct images of either slices or volumes. A slice is a thin volume that is only one voxel thick. A voxel is a small volume element over which the MR signal is averaged, and represents the resolution of the MR image. A voxel may also be referred to as a pixel (picture element) herein if a single slice is considered.

The imaging of bone tissue is in some cases difficult due to the short T2 time present in these highly ordered structures. Typically special pulse sequences are used to image the bone tissue. For example, the journal article Tyler, Damian J., et al. "Magnetic resonance imaging with ultrashort TE (UTE) PULSE sequences: technical considerations." *Journal of Magnetic Resonance Imaging* 25.2 (2007): 279-289 discusses several techniques.

Another approach for imaging bone tissue is to perform image segmentation of magnetic resonance images. U.S. Pat. No. 7,920,730 B2 discloses a method for detecting bone and bone disease using MRI images which includes: detecting and segmenting bone borders using dark bone border intensity information from an MRI image; and detecting bone disease within a segmented image region.

Dixon methods of magnetic resonance imaging include a family of techniques for producing separate water and lipid (fat) images. The various Dixon techniques such as, but not limited to, two-point Dixon methods, three-point Dixon methods, and multi-point Dixon methods are collectively referred to herein as Dixon techniques or methods. The terminology to describe the Dixon techniques is well known and has been the subject of many review articles and is present in standard texts on Magnetic Resonance Imaging. For example, the "Handbook of MRI Pulse Sequences" by Bernstein et al., published by Elsevier Academic Press in 2004, contains a review of some Dixon techniques on pages 857 to 887.

The journal article Koch, Kevin M., et al. "Rapid calculations of susceptibility-induced magnetostatic field perturbations for in vivo magnetic resonance." *Physics in medicine and biology* 51.24 (2006): 6381 discloses the calculation of an approximated solution to Maxwells's equation to predict macroscopic inhomogeneity of the B0 field induced by susceptibility differences in vivo.

SUMMARY OF THE INVENTION

The invention provides for a medical instrument, a method of operating the medical instrument, and a computer program product in the independent claims. Embodiments are given in the dependent claims.

As will be appreciated by one skilled in the art, aspects of the present invention may be embodied as an apparatus, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer executable code embodied thereon.

Any combination of one or more computer readable medium(s) may be utilized. The computer readable medium may be a computer readable signal medium or a computer readable storage medium. A 'computer-readable storage medium' as used herein encompasses any tangible storage medium which may store instructions which are executable by a processor of a computing device. The computer-readable storage medium may be referred to as a computer-readable non-transitory storage medium. The computer-readable storage medium may also be referred to as a tangible computer readable medium. In some embodiments, a computer-readable storage medium may also be able to store data which is able to be accessed by the processor of the computing device. Examples of computer-readable storage media include, but are not limited to: a floppy disk, a magnetic hard disk drive, a solid state hard disk, flash memory, a USB thumb drive, Random Access Memory (RAM), Read Only Memory (ROM), an optical disk, a magneto-optical disk, and the register file of the processor. Examples of optical disks include Compact Disks (CD) and Digital Versatile Disks (DVD), for example CD-ROM, CD-RW, CD-R, DVD-ROM, DVD-RW, or DVD-R disks. The term computer readable-storage medium also refers to various types of recording media capable of being accessed by the computer device via a network or communication link. For example a data may be retrieved over a modem, over the internet, or over a local area network. Computer executable code embodied on a computer readable medium may be transmitted using any appropriate medium, including but not limited to wireless, wire line, optical fiber cable, RF, etc., or any suitable combination of the foregoing.

A computer readable signal medium may include a propagated data signal with computer executable code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

'Computer memory' or 'memory' is an example of a computer-readable storage medium. Computer memory is any memory which is directly accessible to a processor. 'Computer storage' or 'storage' is a further example of a computer-readable storage medium. Computer storage is any non-volatile computer-readable storage medium. In some embodiments computer storage may also be computer memory or vice versa.

A 'processor' as used herein encompasses an electronic component which is able to execute a program or machine executable instruction or computer executable code. References to the computing device comprising "a processor" should be interpreted as possibly containing more than one processor or processing core. The processor may for instance be a multi-core processor. A processor may also refer to a collection of processors within a single computer system or distributed amongst multiple computer systems. The term computing device should also be interpreted to possibly refer to a collection or network of computing devices each comprising a processor or processors. The computer executable code may be executed by multiple processors that may be within the same computing device or which may even be distributed across multiple computing devices.

Computer executable code may comprise machine executable instructions or a program which causes a processor to perform an aspect of the present invention. Computer executable code for carrying out operations for aspects of the present invention may be written in any combination of one or more programming languages, including an object oriented programming language such as Java, Smalltalk, C++ or the like and conventional procedural programming languages, such as the C programming language or similar programming languages and compiled into machine executable instructions. In some instances the computer executable code may be in the form of a high level language or in a pre-compiled form and be used in conjunction with an interpreter which generates the machine executable instructions on the fly.

The computer executable code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described with reference to flowchart illustrations and/or block diagrams of methods, apparatus (systems) and computer program products according to embodiments of the invention. It is understood that each block or a portion of the blocks of the flowchart, illustrations, and/or block diagrams, can be implemented by computer program instructions in form of computer executable code when applicable. It is further understood that, when not mutually exclusive, combinations of blocks in different flowcharts, illustrations, and/or block diagrams may be combined. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

A 'user interface' as used herein is an interface which allows a user or operator to interact with a computer or computer system. A 'user interface' may also be referred to as a 'human interface device.' A user interface may provide information or data to the operator and/or receive information or data from the operator. A user interface may enable input from an operator to be received by the computer and may provide output to the user from the computer. In other words, the user interface may allow an operator to control or manipulate a computer and the interface may allow the computer indicate the effects of the operator's control or manipulation. The display of data or information on a display or a graphical user interface is an example of providing information to an operator. The receiving of data through a keyboard, mouse, trackball, touchpad, pointing stick, graphics tablet, joystick, gamepad, webcam, headset, pedals, wired glove, remote control, and accelerometer are all examples of user interface components which enable the receiving of information or data from an operator.

A 'hardware interface' as used herein encompasses an interface which enables the processor of a computer system to interact with and/or control an external computing device and/or apparatus. A hardware interface may allow a processor to send control signals or instructions to an external computing device and/or apparatus. A hardware interface may also enable a processor to exchange data with an external computing device and/or apparatus. Examples of a hardware interface include, but are not limited to: a universal serial bus, IEEE 1394 port, parallel port, IEEE 1284 port, serial port, RS-232 port, IEEE-488 port, Bluetooth connection, wireless local area network connection, TCP/IP connection, Ethernet connection, control voltage interface, MIDI interface, analog input interface, and digital input interface.

A 'display' or 'display device' as used herein encompasses an output device or a user interface adapted for displaying images or data. A display may output visual, audio, and or tactile data. Examples of a display include, but are not limited to: a computer monitor, a television screen, a touch screen, tactile electronic display, Braille screen, Cathode ray tube (CRT), Storage tube, Bi-stable display, Electronic paper, Vector display, Flat panel display, Vacuum fluorescent display (VF), Light-emitting diode (LED) displays, Electroluminescent display (ELD), Plasma display panels (PDP), Liquid crystal display (LCD), Organic light-emitting diode displays (OLED), a projector, and Head-mounted display.

Magnetic Resonance (MR) data is defined herein as being the recorded measurements of radio frequency signals emitted by atomic spins using the antenna of a magnetic resonance apparatus during a magnetic resonance imaging scan. Magnetic resonance data is an example of medical image data. A Magnetic Resonance (MR) image is defined herein as being the reconstructed two or three dimensional visualization of anatomic data contained within the magnetic resonance imaging data. This visualization can be performed using a computer.

In one aspect the invention provides for a medical instrument. The medical instrument comprises a magnetic resonance imaging system for acquiring magnetic resonance data from a subject within an imaging zone. The magnetic resonance imaging system comprises a main magnet for generating a B0 magnetic field within an imaging zone. The B0 magnetic field is also often referred to as a main magnetic field. The B0 or main magnetic field is a static and uniform magnetic field within the imaging zone which aligns the magnetic spins of various atoms so that magnetic resonance imaging may be performed. The magnetic resonance imaging system further comprises a memory containing machine-executable instructions and pulse sequence commands. The magnetic resonance imaging system further comprises a processor for controlling the medical instrument. Execution of the machine-executable instructions causes the processor to acquire the magnetic resonance data by controlling the magnetic resonance imaging system with the pulse sequence commands. Execution of the machine-executable instructions further causes the processor to receive a subject magnetic susceptibility map of the subject. The subject magnetic susceptibility map could be received in a variety of different ways. The subject magnetic susceptibility map for example may be stored in a memory or a computer storage device of the processor. In other examples the subject magnetic susceptibility map is received by calculating it from a different data source such as a magnetic resonance image.

Execution of the machine-executable instructions further causes the processor to calculate a B0 inhomogeneity map from the magnetic resonance data. The determination of the B0 inhomogeneity map is well known and a variety of different approaches can be taken to determine the B0 inhomogeneity map. For example, the B0 inhomogeneity map may often be determined when performing a Dixon magnetic resonance imaging technique. The advantage of using a Dixon technique to map B0 is that the off-resonance effects resulting from fat which could compromise the quality of an in-vivo B0 map, are intrinsically compensated by the Dixon based reconstruction. A review of common Dixon techniques may for instance be found in the Handbook of MRI Pulse Sequences by Bernstein et al. (see pages 857-887). In principle any multi-gradient-echo sequence which samples multiple echoes after one RF excitation or making several RF excitations and sample one echo shifting at a time may be used. This may often be combined with the various fat suppression magnetic resonance imaging techniques or protocols.

Execution of the machine-executable instructions further cause the processor to calculate a subject B0 magnetic field perturbation from the estimated subject magnetic susceptibility map. For example if a volumetric magnetic resonance imaging protocol is being performed such a subject specific magnetic susceptibility map can be derived by simple means of segmentation. The simplest model could consist out of two compartments (tissue and air) represented by their corresponding susceptibility values. More complex tissue/susceptibility models are conceivable. Furthermore, the operating field strength (B0) is known. From this it is straight forward to calculate the subject B0 magnetic field perturbation from the subject magnetic susceptibility map using known techniques or electrodynamics. Execution of the machine-executable instructions further cause the processor to calculate a residual B0 magnetic field perturbation by subtracting the subject B0 magnetic field perturbation from the B0 inhomogeneity map. In this operation the value of the calculated subject B0 magnetic field perturbation is subtracted from the B0 inhomogeneity map and this results in the residual B0 magnetic field perturbation.

The residual B0 magnetic field perturbation is a perturbation to the B0 magnetic field which cannot be accounted for by the estimated subject magnetic susceptibility map. It is assumed that this perturbation may result from bone tissue, which does not give significant signal in conventional MRI and was not subject of any segmentation. Next execution of the machine-executable instructions further cause the processor to calculate a bone map from the residual B0 magnetic field perturbation. Knowing quantitatively the residual B0 magnetic field perturbation enables the direct calculation of a distribution of bone tissue which could result in this residual B0 magnetic field perturbation. For example the distribution of bone within the subject may be referred to as a bone map. The bone map may be calculated by solving for or iteratively determining the distribution of bone or bone map which results in the residual B0 magnetic field perturbation.

The medical instrument may have for example the benefit that the location of bone tissue can be inferred using normal or conventional magnetic resonance imaging protocols.

In another embodiment execution of the machine-executable instructions further cause the processor to reconstruct at least a portion of the magnetic resonance data into at least one subject magnetic resonance image. Execution of the machine-executable instructions further causes the processor to calculate a subject model by segmenting the subject magnetic resonance image. Execution of the machine-executable instructions further cause the processor to construct the subject magnetic resonance susceptibility map from the subject model. The construction of the subject susceptibility map could be done in a variety of different ways. In one case a simple magnetic resonance image, for example the proton density image, could be used to fit a model which has includes assumptions about the distribution of the magnetic susceptibility within the subject. For example the model may be fit to the magnetic resonance data which provides data or a predication of the type of tissue distribution within the subject. A knowledge of the spatial dependence of particular tissue types allows the direct construction of the subject magnetic susceptibility map.

In one example the pulse sequence commands are for a single magnetic resonance imaging protocol. In other examples the pulse sequence commands could be for performing more than one magnetic resonance imaging protocol.

In another embodiment the pulse sequence commands comprise commands for acquiring the magnetic resonance imaging data according to a Dixon magnetic resonance imaging protocol. The at least one subject magnetic resonance image comprises at least one fat image and at least one water image. The subject model comprises a fat portion and a water portion. The subject magnetic susceptibility map is calculated by adding or assigning (the spatial contribution to magnetic resonance susceptibility from the fat portion and from the water portion. The magnetic susceptibility of fat and water within the subject may be known.

In another embodiment calculating the subject model comprises determining the spatial dependence of water and fat in the subject using the at least one fat image and the at least one water image. The spatial dependence of the water and fat can be expressed in different forms. For example the spatial dependence of water may be one mapping and the spatial dependence of fat may be another mapping. In other examples the spatial dependence is expressed in a ratio.

In another embodiment execution of the machine-executable instructions further cause the processor to calculate a spatial bone distribution by applying an inverted Green's function to the residual B0 magnetic field perturbation. The bone map is at least partially calculated from the spatial bone distribution.

The inverted Green's function in some examples may be an inverted Green's dipole function. The inverted Green's function could also be referred to as a Green's deconvolution.

In some cases the spatial bone distribution is the bone map. In other cases the spatial bone distribution is used in calculating the bone map.

In another embodiment execution of the instructions further cause the processor to first estimate a spatial bone distribution. Execution of the machine-executable instructions further cause the processor to iteratively refine the spatial bone distribution by applying a Green's function to the spatial bone distribution and then compare the resulting estimated B0 magnetic field perturbation to the residual B0 magnetic field perturbation in an optimization algorithm. The optimization algorithm can then add or remove small portions of bone tissue to the spatial bone distribution. The subsequent spatial bone distribution can then be used to calculate a new estimated B0 magnetic field perturbation. This process is then repeated until the estimated B0 magnetic field perturbation converges, within a predetermined measure, to the residual B0 magnetic field perturbation.

The bone map is at least partially calculated from the spatial bone distribution. Instead of using an inverted Green's function an initial guess as to where the bone tissue is in the form of the preliminary spatial bone distribution then using a forward Green's function to calculate a residual B0 magnetic field perturbation. The resulting calculated residual B0 magnetic field perturbation is within a predetermined distance or criterion of the actual residual B0 magnetic field perturbation then the algorithm stops. If not then the spatial location of bone tissue is adjusted to try to correct the spatial bone distribution. This can be performed iteratively until a satisfactory solution is found for the spatial bone distribution.

In another embodiment execution of the instructions further cause the processor to calculate the bone map by segmenting the at least one subject magnetic resonance image. The calculating of the segmented bone image comprises weighting the segmentation using the spatial bone distribution. In this embodiment the bone map is not directly calculated from the spatial bone distribution but the spatial bone distribution is used to weight the image segmentation. This may be particularly useful in plotting the location of the bone tissue. For example bone typically has other tissues in contact with it. These tissues may be visible in a magnetic resonance imaging image. The difficulty is that there may be air cavities, bubbles or other structures within a subject which have regions that do not emit a very strong magnetic resonance signal that is imaged. Using the spatial bone distribution to perform a weighting during the segmentation may reduce the chance that a region is falsely selected as containing bone tissue.

In another embodiment execution of the instructions further cause the processor to calculate the bone map by segmenting the at least one subject magnetic resonance image and to adjust the bone map using the spatial bone distribution. In this example the bone map is calculated primarily by segmenting the subject magnetic resonance image. The boundaries or other locations in the bone map are then corrected using the spatial bone distribution.

In another embodiment execution of the instructions further cause the processor to calculate a radiation attenuation map using the bone map and the subject model. The radiation attenuation map as used herein is a 3D distribution of tissue which may be used to calculate the attenuation of ionizing radiation through the subject. Combining the subject model and the bone map may result in a more accurate radiation attenuation map. This may be useful for example during radiation planning or in other nuclear medical imaging techniques such as positron emission tomography or single photon emission tomography.

In another embodiment the medical system further comprises a nuclear medical imaging system for acquiring a nuclear medical image of at least the imaging zone. Execution of the machine-executable instructions further causes the processor to acquire nuclear medical imaging data from the imaging zone. Execution of the machine-executable instructions further causes the processor to reconstruct the nuclear medical image using the nuclear medical imaging data and the radiation attenuation map. This embodiment may be beneficial because the subject can have the radiation attenuation map acquired or determined and without moving a nuclear medical imaging technique may be performed.

Examples of a nuclear medical imaging system include a positron emission tomography system or a single photon emission tomography system.

In another embodiment execution of the machine-executable instructions further cause the processor to receive a treatment plan. Execution of the machine-executable instructions further cause the processor to generate radiation therapy system control commands using the treatment plan and the radiation attenuation map.

In another embodiment the medical instrument further comprises a radiation therapy system for irradiating a target within the imaging zone. Execution of the machine-executable instructions further cause the processor to control the radiation therapy system with the radiation therapy system control commands.

In another embodiment execution of the machine-executable instructions further cause the processor to receive a background B0 magnetic field map descriptive of the B0 magnetic field within the imaging zone. Execution of the machine-executable instructions further cause the processor to correct the B0 inhomogeneity map with the background B0 magnetic field map before calculating the residual B0 magnetic field perturbation. This embodiment may be beneficial when there are large inhomogeneities in the B0 magnetic field intrinsic to the magnetic resonance imaging system. It may also be useful in the boundaries of the imaging zone where the B0 magnetic field is more inhomogeneous.

The background B0 magnetic field can be obtained in different ways. The information about the main magnetic field distribution without the patient in place can be obtained for example from, but not limited to:
- the shim plot measured during system installation or
- some dedicated B0-map phantom measurements (using a water filled sphere) or
- other field probes/field measuring approaches.

In another aspect the invention provides for a method of operating the medical instrument. The medical instrument comprises a magnetic resonance imaging system for acquiring magnetic resonance data form a subject within an imaging zone. The magnetic resonance imaging system comprises a main magnet for generating a B0 magnetic field within an imaging zone. The method comprises the step of acquiring the magnetic resonance data by controlling the magnetic resonance imaging system with the pulse sequence commands. The method further comprises receiving a subject magnetic susceptibility map of the subject. The method further comprises calculating a B0 inhomogeneity map from the magnetic resonance data. The method further comprises calculating a subject B0 magnetic field perturbation from the subject magnetic susceptibility map. The method further comprises calculating a residual B0 magnetic field perturbation by subtracting the subject B0 magnetic field perturbation from the B0 inhomogeneity map. The method further comprises calculating a bone map from the residual B0 magnetic field perturbation.

In another aspect the invention provides for a computer program product comprising machine-executable instructions for execution by a processor controlling the medical instrument. The medical instrument comprises a magnetic resonance imaging system for acquiring magnetic resonance data from a subject within an imaging zone. The magnetic resonance imaging system comprises a main magnet for generating a B0 magnetic field within an imaging zone. Execution of the machine-executable instructions causes the processor to acquire the magnetic resonance data by controlling the magnetic resonance imaging system with the pulse sequence commands. Execution of the machine-executable instructions further causes the processor to receive a subject magnetic susceptibility map of the subject. Execution of the machine-executable instructions further cause the processor to calculate a B0 inhomogeneity map from the magnetic resonance data.

Execution of the machine-executable instructions further cause the processor to calculate a subject B0 magnetic field perturbation from the subject magnetic susceptibility map. Execution of the machine-executable instructions further cause the processor to calculate a residual B0 magnetic field perturbation by subtracting the subject B0 magnetic field perturbation from the B0 inhomogeneity map. Execution of the machine-executable instructions further cause the processor to calculate a bone map from the residual B0 magnetic field perturbation.

It is understood that one or more of the aforementioned embodiments of the invention may be combined as long as the combined embodiments are not mutually exclusive.

BRIEF DESCRIPTION OF THE DRAWINGS

In the following preferred embodiments of the invention will be described, by way of example only, and with reference to the drawings in which.

DETAILED DESCRIPTION OF THE EMBODIMENTS

Like numbered elements in these figures are either equivalent elements or perform the same function. Elements which have been discussed previously will not necessarily be discussed in later figures if the function is equivalent.

Figure 1:
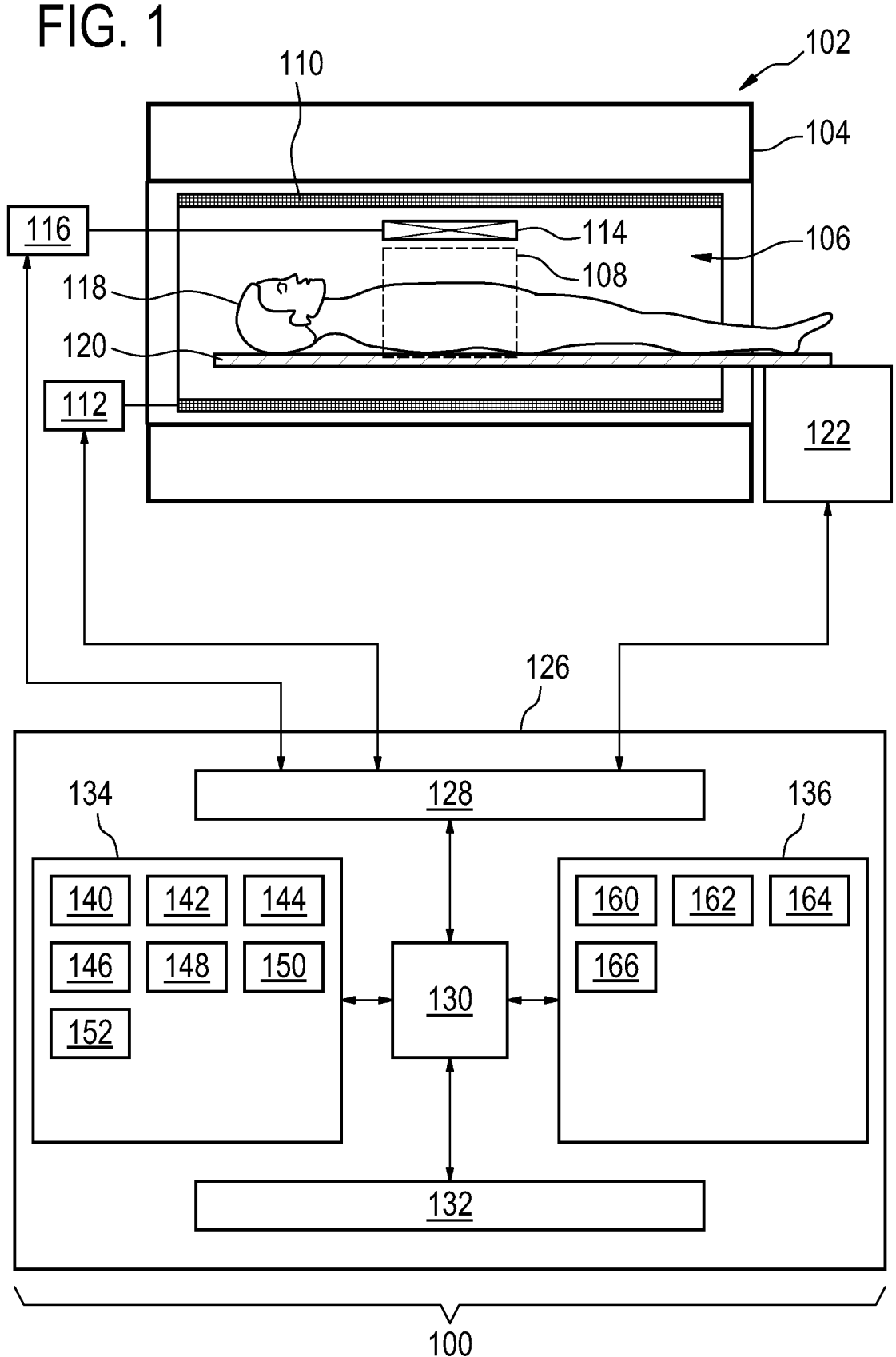
FIG. 1 illustrates an example of a medical instrument.

FIG. 1 shows an example of a medical instrument 100. The medical instrument 100 comprises a magnetic resonance imaging system 102. The magnetic resonance imaging system 102 comprises a magnet 104. The magnet 104 is a superconducting cylindrical type magnet 104 with a bore 106 through it. The use of different types of magnets is also possible; for instance it is also possible to use both a split cylindrical magnet and a so called open magnet. A split cylindrical magnet is similar to a standard cylindrical magnet, except that the cryostat has been split into two sections to allow access to the iso-plane of the magnet, such magnets may for instance be used in conjunction with charged particle beam therapy. An open magnet has two magnet sections, one above the other with a space in-between that is large enough to receive a subject: the arrangement of the two sections area similar to that of a Helmholtz coil. Open magnets are popular, because the subject is less confined. Inside the cryostat of the cylindrical magnet, there is a collection of superconducting coils. Within the bore 106 of the cylindrical magnet 104 there is an imaging zone 108 where the magnetic field is strong and uniform enough to perform magnetic resonance imaging.

Within the bore 106 of the magnet there is also a set of magnetic field gradient coils 110 which is used for acquisition of magnetic resonance data to spatially encode magnetic spins within the imaging zone 108 of the magnet 104. The magnetic field gradient coils 110 are connected to a magnetic field gradient coil power supply 112. The magnetic field gradient coils 110 are intended to be representative. Typically magnetic field gradient coils 110 contain three separate sets of coils for spatially encoding in three orthogonal spatial directions. A magnetic field gradient power supply supplies current to the magnetic field gradient coils. The current supplied to the magnetic field gradient coils 110 is controlled as a function of time and may be ramped or pulsed.

Adjacent to the imaging zone 108 is a radio-frequency coil 114 for manipulating the orientation of magnetic spins within the imaging zone 108 and for receiving radio transmissions from spins also within the imaging zone 108. The radio frequency antenna may contain multiple coil elements. The radio frequency antenna may also be referred to as a channel or antenna. The radio-frequency coil 114 is connected to a radio frequency transceiver 116. The radio-frequency coil 114 and radio frequency transceiver 116 may be replaced by separate transmit and receive coils and a separate transmitter and receiver. It is understood that the radio-frequency coil 114 and the radio frequency transceiver 116 are representative. The radio-frequency coil 114 is intended to also represent a dedicated transmit antenna and a dedicated receive antenna. Likewise the transceiver 116 may also represent a separate transmitter and receiver. The radio-frequency coil 114 may also have multiple receive/ transmit elements and the radio frequency transceiver 116 may have multiple receive/transmit channels.

Within the bore 106 of the magnet 104 there is a subject support 120 which is attached to an optional actuator 122 that is able to move the subject support and the subject 118 through the imaging zone 108. The transceiver 116, the magnetic field gradient coil power supply 112 and the actuator 122 are all seen as being connected to a hardware interface 128 of computer system 126.

The contents of the computer storage 134 and the computer memory 136 may be interchangeable. In some examples the contents of the computer storage 134 may be duplicated in the computer memory 136.

The computer storage 134 is shown as containing pulse sequence commands 140. The pulse sequence commands 140 are commands or data which may be converted into commands to create instructions for controlling the magnetic resonance imaging system 102 to acquire magnetic resonance data. The computer storage 134 is further shown as containing magnetic resonance data 142 that was acquired using the pulse sequence commands 140. The computer storage 134 is further shown as containing a subject magnetic susceptibility map 144 that was received. It may for example have been calculated by the processor 130 from other data or it may have been input or received via network or other storage device. The computer storage 134 is further shown as containing a B0 inhomogeneity map 146 that was calculated from the magnetic resonance data 142. In one particular example the pulse sequence commands 140 are Dixon pulse sequence commands and the B0 inhomogeneity map 146 is calculated during the process of processing the magnetic resonance data 142 according to a Dixon magnetic resonance protocol. The computer storage 134 is further shown as containing subject B0 magnetic field perturbation 148. The subject B0 magnetic field perturbation was calculated from the subject magnetic susceptibility map 144. The computer storage 134 is further shown as containing a residual B0 magnetic field perturbation 150 that was calculated by subtracting the subject B0 magnetic field perturbation 148 from the B0 inhomogeneity map 146. The computer storage is further shown as containing a bone map 152 that was calculated from the residual B0 magnetic field perturbation 150.

The computer memory 136 is further shown as containing a control module 160. The control module 160 contains instructions that enable the processor 130 to control and operate the entire medical instrument 100 including the magnetic resonance imaging system 102. For example the control module 160 may enable the processor 130 to use the pulse sequence commands 140 to acquire the magnetic resonance data 142. The computer memory 136 is further shown as containing an image reconstruction module 162. The image reconstruction module 162 contains computer code or instructions which enable the processor 130 to reconstruct and extract data from the magnetic resonance data 142. This may include processing the magnetic resonance data 142 to various imaging protocols and performing Fourier transforms.

The computer memory 136 is shown as containing a differential equation module 164 that enables the processor 130 to apply various spherical and differential type equations for processing data. For example the differential equation module 164 may enable the processor 130 to process various data according to Green's or inverse Green functions. The computer memory 136 is further shown as containing an image processing module 166. The image processing module 166 enables the processor 130 to perform image processing techniques for modifying images and also to perform various mathematical operations on arrays and large bundles of data. The contents of the computer storage 134 and the computer memory 136 may be duplicated in each other or various items shown in one may be switched or stored in the other.

Figure 2:
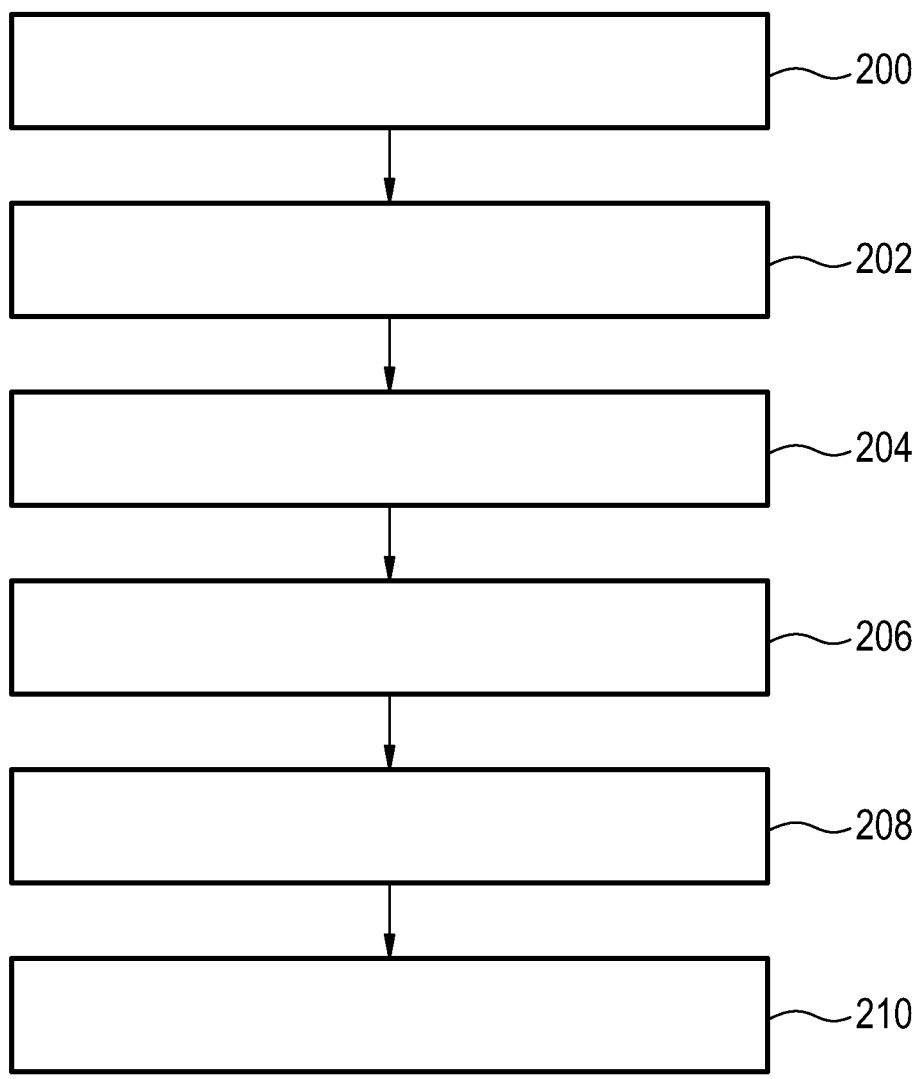
FIG. 2 shows a flow chart which illustrates a method of operating the medical instrument of FIG. 1.

FIG. 2 shows a flow diagram which illustrates a method of operating the medical instrument 100 of FIG. 1. First in step 200 the magnetic resonance data 142 is acquired by controlling the magnetic resonance imaging system 102 with the pulse sequence commands 140. Next in step 202 the subject magnetic susceptibility map 144 is received. Next in step 204 the B0 inhomogeneity map 146 is calculated from the magnetic resonance data 142. Next in step 206 the subject B0 magnetic field perturbation 148 is calculated from the subject magnetic susceptibility map 144. In step 208 the residual B0 magnetic field perturbation 150 is calculated by subtracting the subject B0 magnetic field perturbation 148 from the B0 inhomogeneity map 146. Finally in step 210 the bone map 152 is calculated from the residual B0 magnetic field perturbation 150. In some examples the bone map may be calculated directly from the residual B0 magnetic field perturbation for example using an inverse Green's function. In other cases the bone map may be calculated in conjunction with various image processing or segmentation techniques also in an iterative procedure, in which also the initially estimated body susceptibility map, may be subject of optimization. The subject B0 magnetic field perturbation and the residual B0 magnetic field perturbation are both mappings means three-dimensional datasets.

MRI is usually not able to detect cortical bone, because solid structures exhibit very short T2s. However, these kind of solid tissues, even if MR-invisible, influence the MRI signal in their neighborhood via their magnetic susceptibility. The corresponding magnetic dipole effects influence the effective magnetic field also in areas rather distant form the actual susceptibility source.

Therefore, examples may use a measured B0 map, some object information and an appropriate "dipole inversion" to localize cortical bone (or material which differs in susceptibility from water-rich tissue). This could be a very helpful to localize cortical bone in radiation treatment planning or to support PET attenuation map estimation because measured B0 maps can be obtained as a byproduct of a Dixon scan.

There is a wish to use MRI data to support radiation treatment planning. In this procedure, knowledge of the location of bone tissue is important, because bone exhibits stronger radiation absorption than normal tissue. The same holds for attenuation correction in PET applied to improve PET image reconstruction. To identify bones, UTE can be employed to partly visualize short T2 components which can be attributed to bone. However, current UTE technology is not able to provide full information on rigid, calcified bone, i.e. cortical bone, which contains only few MR detectable protons. To complement UTE, Dixon imaging has been proposed. It allows separating water and fat, with the latter being a substantial component of bone marrow. In this way, it provides additional information to indirectly identify bone tissue. Nevertheless, much prior knowledge and anatomy-guided modeling is still required to rule out potential ambiguities. For example, fat is not uniquely present in bone marrow, it is found everywhere in the body, making sophisticated image processing necessary to indirectly localize bone. Such a procedure may fail if the particular patient differs in anatomy significantly from the employed anatomical model.

Some examples may recycle the field map available from Dixon imaging, or from any other source. Even if the bone tissue does not contribute to the measured MR signal, due to the too long TEs chosen, its susceptibility properties do influence the B0 field in the surroundings. This influence can be seen with MR via the water or fat signal present around the bone tissue. Please note that in the following a 3D B0 map is considered. The measured B0 map has actually two major components:

$$B_{0meas}(r) = B_{0vacuum}(r) + B_{0body\_susc}(r) \quad [1]$$

$B_{0\ vacuum}(r)$ can be estimated during system installation or from bare shim plots or other measurements and represents the main field inhomogeneity with no patient present. Alternatively, it can be assumed that the effect of a bad shim is spatially smooth and can be removed by appropriate fitting or bias correction. Assuming that this operation is successful one can obtain from the measured B0 map a $B'_{0\ meas}(r)$ that is dominated by body susceptibility contributions:

$$B'_{0meas}(r) = B_{0body\_susc}(r) \quad [2]$$

It is important to note that the effect of the body susceptibility on the induced main field inhomogeneities ($B0\ body\_susc(r)$) can be predicted by appropriate simulations. The $B_{0\ body\_susc}(r)$ can be approximated as a convolution (*) of the body susceptibility distribution $S(r)$ with the Green's-dipole function ($G(r)$).

$$B_{0body\_susc}(r) = S(r) * G(r) \quad [3]$$

$$\text{with } G_{z,3D}(\vec{r} - \vec{r}') = \frac{1}{4\pi}\left(\frac{3(z-z')^2}{|\vec{r}-\vec{r}'|^5} - \frac{1}{|\vec{r}-\vec{r}'|^3}\right)$$

Different tissues types have different susceptibility values ($X_{water} = -9.2$ ppm, $X_{fat} = -9.7$ ppm, $X_{bone} = -12.8$ ppm, $X_{air} = 0$ ppm (numbers might be imprecise)). The susceptibility of water and fat are almost identical, but the one of air and bone differ significantly. So based on the 3D Dixon water/fat (magnitude) images and appropriate thresholding one is able to form a simple 3D body susceptibility map. This X map defines at every pixel the corresponding susceptibility value either of water, fat or air. The map does not contain bone because it does not give signal in the magnitude image. This procedure can be simplified, due to the similarity of water and fat susceptibility values: each voxel within the body gets an average (water/fat) susceptibility value unless it is air (X=0). Voxels outside are also set to zero. This way a simple binary body mask is created, which can be used to estimate/simulate the body susceptibility induced field contribution ($B_{0\ body\_susc\_sim}(r)$). Due to the fact that bone was not considered in the simulation, the difference map $$B_{0diff}(r) = B'_{0meas}(r) - B_{0body\_susc\_sim}(r) \quad [4]$$

is dominated by field contributions of the remaining bone. The spatial contribution of the bone ($Bone(r)$) which can be modelled by $$B_{0diff}(r) = B_{one}(r) * G(r) \quad [5]$$

can be obtained by inverting Eq. 5.

$$B_{one}(r) = B_{0diff}(r) * G^{-1}(r) \quad [6]$$

Using appropriate regularization this could be solved in the Fourier domain using FFT or better via algebraic means writing the problem in Eq. [6] in matrix vector notation. The problem can then be solved via the appropriate pseudo-inverse or if this is not feasible via an iterative approach.

A 3D B0 map may be obtained from a 3D Dixon scan. The static background gradients (B0 vacuum) are removed from the map and an appropriate filtering/bias correction is done on top to isolate the susceptibility dominated field contributions (see Flow chart below in FIG. 3). Using a water-model forward susceptibility simulation and calculating the difference to the measured map, Greens de-convolution gives the location of those components which did not contribute to the MR signal in the MRI measurement (see FIG. 4. below). This way bone tissue could be localized.

Figure 3:
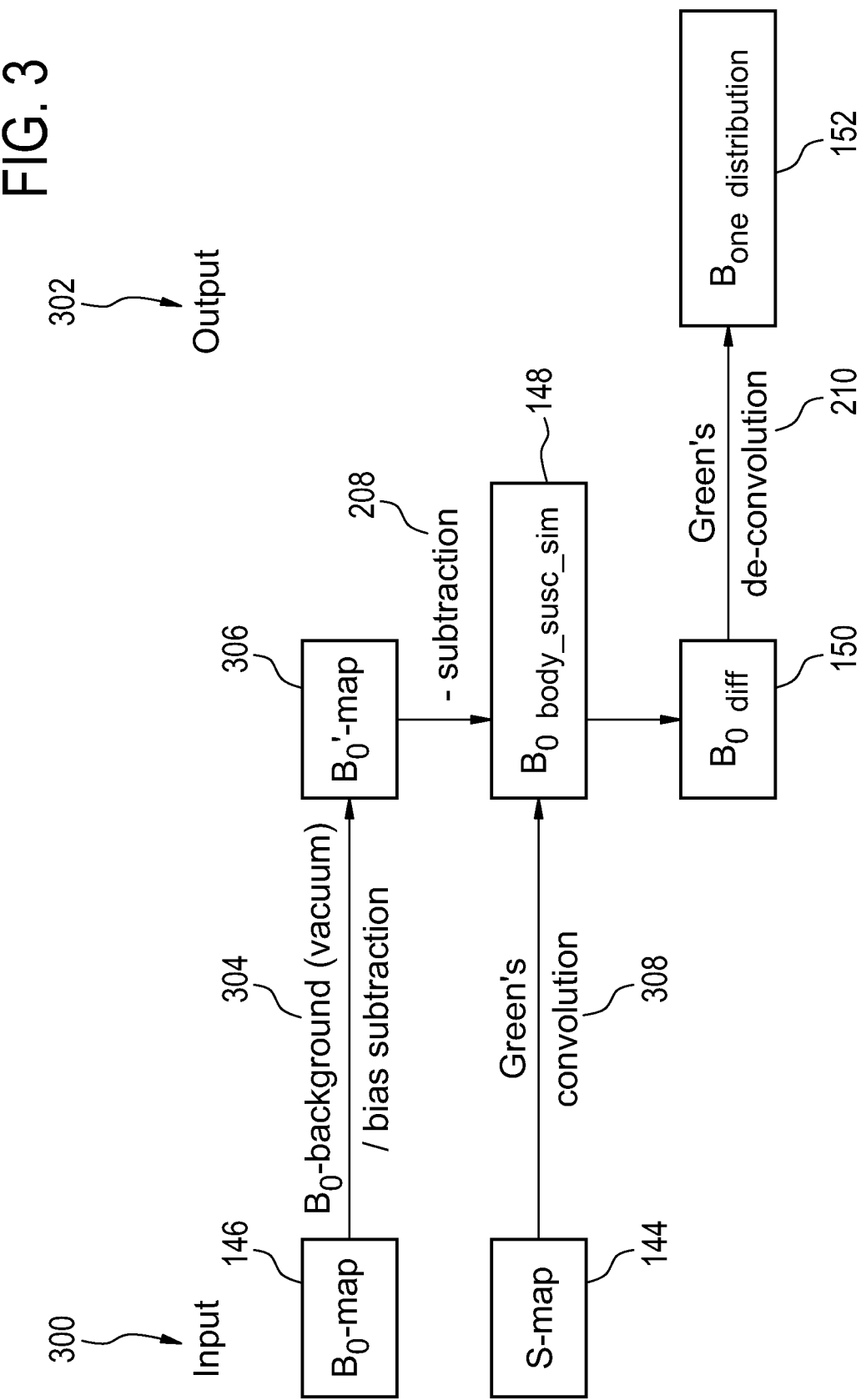
FIG. 3 shows a flow chart which illustrate a further example of a method.

FIG. 3 shows a further flowchart which illustrates a method of calculating a bone map or distribution. In FIG. 3 the method has two inputs; these are the B0 inhomogeneity map 146 and the subject magnetic susceptibility map 144 which is labeled S-map. The flowchart in FIG. 3 shows optional processing of the B0 inhomogeneity map. If a background B0 map that is without the subject present is known then the B0 background map 304 can then be subtracted to calculate a corrected B0 inhomogeneity map 306. If step 304 is not performed then the B0 inhomogeneity map 146 can be used in place of the corrected B0 inhomogeneity map 306. Step 304 is optional if the background inhomogeneity is neglectable. The flowchart in FIG. 3 further shows that the subject magnetic susceptibility map 144 is processed via a Green's convolution 308 to calculate the subject B0 magnetic field perturbation 148. The flowchart further shows that the subject B0 magnetic field perturbation 148 is subtracted 208 from the corrected B0 inhomogeneity map 306. This results in the residual B0 magnetic field perturbation 150. The flowchart then shows that the bone map 152 is calculated from the residual B0 magnetic field perturbation using a Green's deconvolution 210.

FIG. 3. shows a flow chart of the basic idea of the bone detection approach. Input data are a measured B0 map and a tissue map S which can be derived from 3D magnitude MRI data. The first could be corrected for not body-induced susceptibility effects using prior knowledge etc., while S can be used to estimate the susceptibility effects. The differences of the measured and the simulated B0 maps reflect the contributions of invisible tissue which was not considered in the simulation. By appropriate de-convolution the corresponding signal can be localized.

Figure 4:
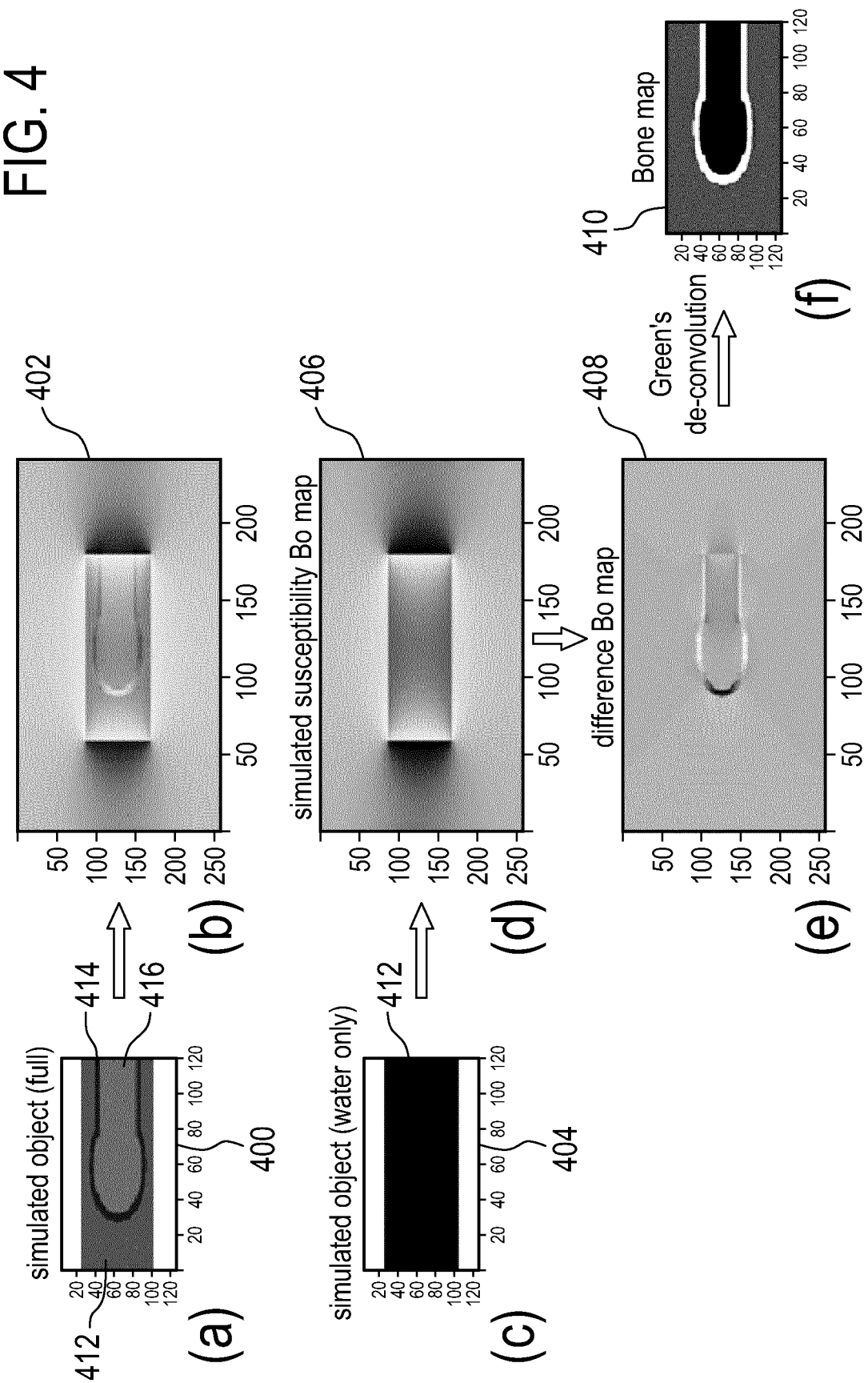
FIG. 4 shows images from a simulation.

FIG. 4 shows a series of simulations which were used to test a method of calculating a bone map 410. Box 400 shows a simulated object which consists of water 412, a bone inside consisting of a layer of cortical bone 414 which encapsulates bone marrow 416. The object in image 400 was then used to calculate a body-induced susceptibility map 402. This was done to mimic a B0 measurement result. For the sake of simplicity a water bath 412 is shown in image 404. This was used to calculate the body-induced susceptibility map for only water 412. This result is shown in image 406. This functions as a reference magnetic resonance image. The difference between images 402 and 406 are shown in the difference B0 map 408. The difference B0 map 408 is analogous to the residual B0 magnetic field perturbation 150 of FIG. 1. FIG. 4 then shows that the bone map 410 is constructed by performing a Green's deconvolution on the difference B0 map 408.

Figure 5:
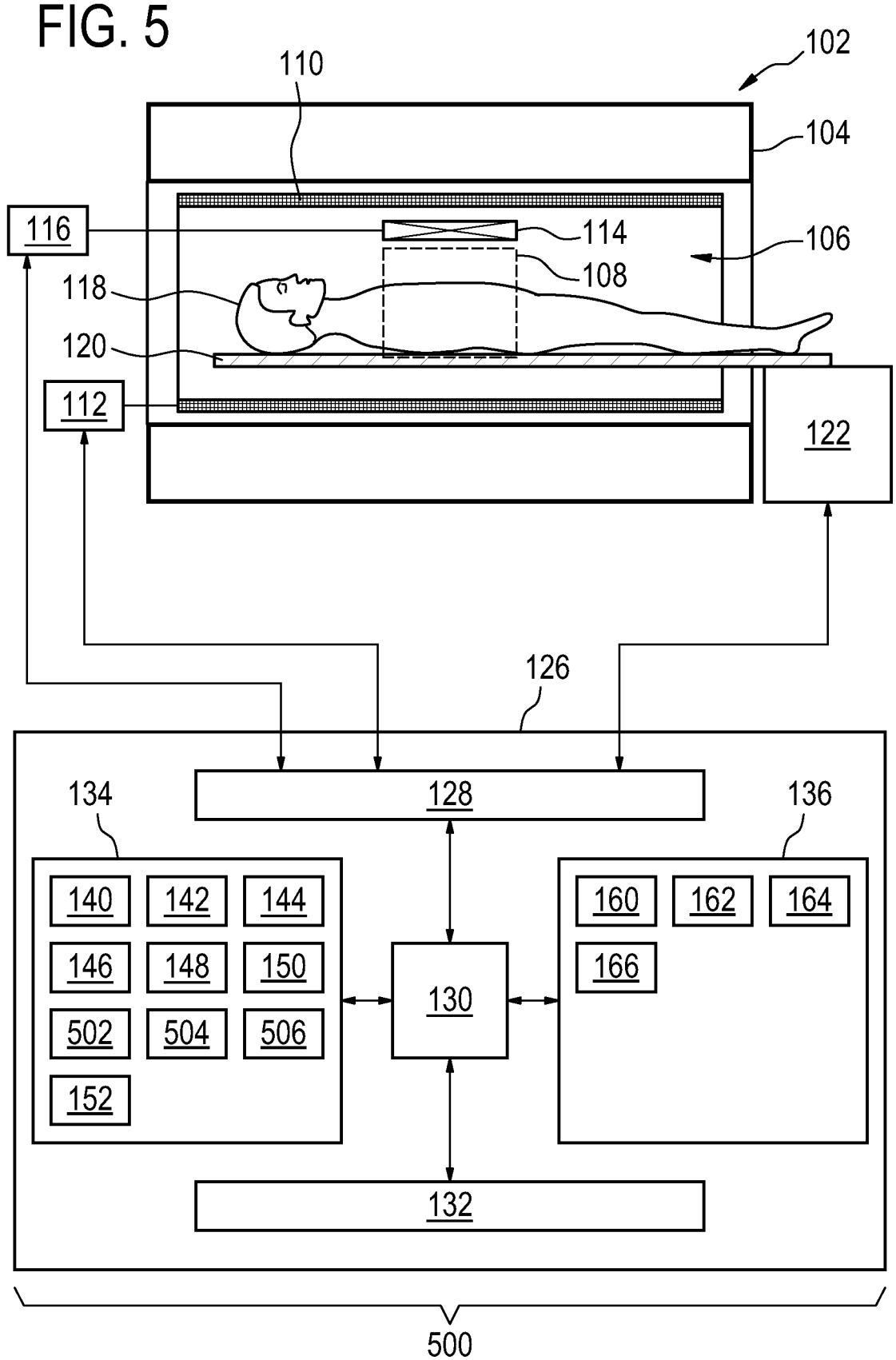
FIG. 5 illustrates a further example of a medical instrument.

FIG. 5 shows a further example of the medical instrument 500. The example shown in FIG. 5 is very similar to the example shown in FIG. 1 with several additions. In this example the pulse sequence commands 140 are for a Dixon magnetic resonance imaging protocol. The magnetic resonance data 142 is processed into the B0 inhomogeneity map 146 and a fat image 502 and a water image 504. The water image 504 and the fat image 502 are used to construct a subject model 506. The subject model 506 has the spatial dependence of water and fat in the subject as a function of position. The processor then uses the subject model 506 to calculate the subject magnetic susceptibility map 144 by assigning a spatial contribution to the magnetic susceptibility from the fat and water as defined in the subject model 506.

Figure 6:
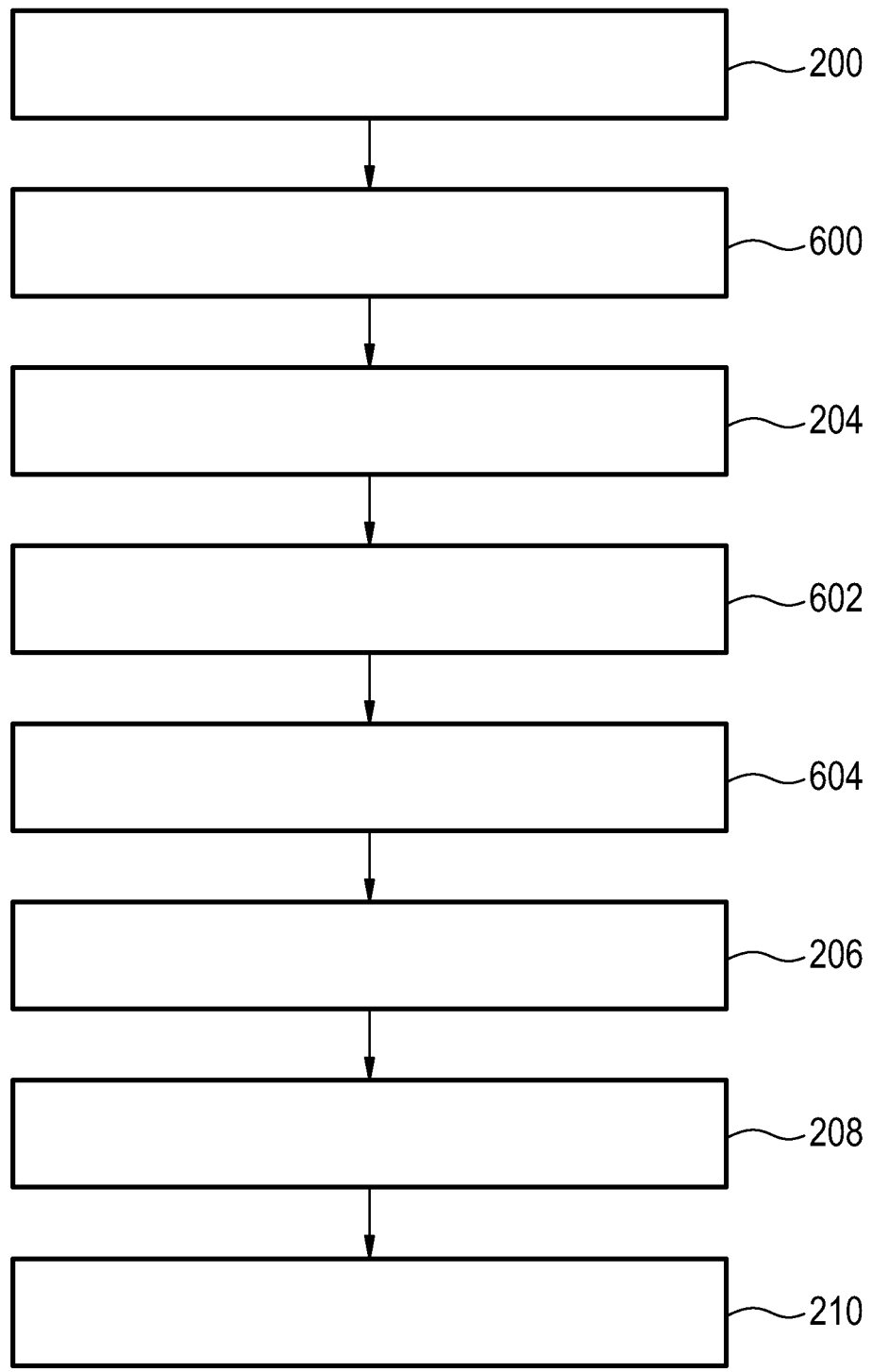
FIG. 6 shows a flow chart which illustrates a method of operating the medical instrument of FIG. 5.

FIG. 6 shows a flowchart which illustrates a method of operating the medical instrument 500 of FIG. 5. The method shown in FIG. 6 is similar to that shown in FIG. 2. Step number 202 in FIG. 2 has been replaced with steps 600, 602 and 604. The method starts in step 200 as identical in FIG. 2. Next step 600, the magnetic resonance data 142 is reconstructed into a fat image 502 and a water image 504. This is done by following the Dixon magnetic resonance imaging protocol. When following this protocol step 204 is also performed. In step 204 the B0 inhomogeneity map 146 is also calculated.

Next in step 602 a subject model 506 is calculated by segmenting the fat image 502 and the water image 504. The subject model 506 may also be calculated by using the fat image 502 and the water image 504 without segmentation by simply using a calculated percentage of fat and water in each voxel. In step 604 the subject magnetic susceptibility map 144 is calculated from the subject model 506. Step 604 is equivalent to providing the subject magnetic susceptibility map in step 202. Next, after performing step 604, the method proceeds to steps 206, 208 and 210 which are identical with those shown in FIG. 2.

In another aspect it is possible to combine the cortical bone localization approach with any kind of model based segmentation. The measured MR data, preferable a mentioned water/fat resolved Dixon data set, which furthermore allows generating a B0-map, is considered here. The B0-map is subjected to the mentioned procedure to estimate bone location and shape etc. due to "quantitative" susceptibility mapping. The information about bone location and shape is used to improve model based segmentation. This can be achieved in the following way:

Based on the water, the fat or on both data, segmentation can be performed which might also include the use of appropriately trained body models with different degrees of detail (organs, bones, potential implants, etc.), which can be matched to the actual patient anatomy. As a result of this segmentation process the different tissue types can be automatically annotated with their corresponding susceptibility values. Using a forward simulation based on the found annotated segmentation results a virtual Bo map can be estimated which can be compared to the measured (experimental one) after applying some static main magnetic field related corrections. Based on the residuals, the differences between the estimated and the experimental B0-maps, the segmentation results can be validated or improved.

For the improvement an iterative procedure using an appropriate penalty function (this function could be $L_2$-norm based, or could also contain sparsity aspects employing a $L_1$- or $L_0$-norm) is conceived. In this function, the corresponding problem can simply be sketched like in the following equation (without loss of generality):

$$S_{egm}(r) : \arg\min\{|W-w(S_{egm})|^2+|W-f(S_{egm})|^2+\alpha|S_{egm}(r) \\ *G(r)-B_{0meas/corr}|^\varphi\} \quad [7]$$

In this formula $S_{egm}(r)$ denotes the segmentation result or more precisely the map generated form the segmentation result (containing different susceptibility values for different tissue classes) which is subjected to the minimization of the three terms given. The operators w( ) and f( ) extract the corresponding water and fat parts from the Dixon MR images using the segmentation result, while W, and F represent the measured water and fat images and the measured, main field corrected B0-map/corr, respectively. The first two $L_2$ terms denote in a very simple form the general segmentation problem, finding sufficient agreement between the water and fat containing parts of the model and the corresponding imaging data. The terms $w(S_{egm})$ and $f(S_{egm})$ form two important components of the entire segmentation result which are elements of $S_{egm}$ which firms also as a kind of tissue susceptibility map. Using the convolution of the tissue susceptibility map with the Greens dipole function results in the tissue induced susceptibility map which has to match the experimental static field corrected B0 data which is moderated by the regularization parameter $\alpha$.

Using a problem as formulated in Eq. 7 or using a similar one is able to improve segmentation results. Incorporating appropriate knowledge about the potential presence of other material with other susceptibility values (like metallic or ceramic implants) which also do not give rise to a direct MR visible signal in the MR could further allow to localize those objects inside the body also with the help of model based segmentation (including prior knowledge about shape and composition as well).

While the invention has been illustrated and described in detail in the drawings and foregoing description, such illustration and description are to be considered illustrative or exemplary and not restrictive; the invention is not limited to the disclosed embodiments.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measured cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

LIST OF REFERENCE NUMERALS

100 medical instrument
102 magnetic resonance system
104 magnet
106 bore of magnet
108 measurement zone or imaging zone
110 magnetic field gradient coils
112 magnetic field gradient coil power supply
114 radio-frequency coil
116 transceiver
118 subject
120 subject support
122 actuator
125 slices
126 computer system 128 hardware interface
130 processor
132 user interface
134 computer storage
136 computer memory
140 pulse sequence commands
142 magnetic resonance data
144 subject magnetic susceptibility map
146 B0 inhomogeneity map
148 subject B0 magnetic field perturbation
150 residual B0 magnetic field perturbation
152 bone map
160 control module
162 image reconstruction module
164 differential equation module
166 image processing module
200 acquire the magnetic resonance data by controlling the magnetic resonance imaging system with the pulse sequence commands
202 receive a subject magnetic susceptibility map of the subject
204 calculate a B0 inhomogeneity map from the magnetic resonance data
206 calculate a subject B0 magnetic field perturbation from the subject magnetic susceptibility map
208 calculate a residual B0 magnetic field perturbation by subtracting the subject B0 magnetic field perturbation from the B0 inhomogeneity map
210 calculate a bone map from the residual B0 magnetic field perturbation
300 input
302 output
304 subtract B0 background map
306 corrected B0 inhomogeneity map
308 Green's convolution
400 image of simulated object
402 calculated body-induced susceptibility map of object in image 400
404 water only image
406 calculated body-induced susceptibility map of water in image 406
408 difference between images 402 and 406
410 bone map
412 water
414 cortical bone
416 bone marrow
502 fat image
504 water image
506 subject model
600 the magnetic resonance data is reconstructed into a fat image and a water image
602 subject model is calculated by segmenting the fat image and the water image
604 the subject magnetic susceptibility map is calculated from the subject model

The invention claimed is:

1. A medical instrument, wherein the medical instrument comprises a magnetic resonance imaging system for acquiring magnetic resonance data from a subject within an imaging zone, wherein the magnetic resonance imaging system comprises:
  a main magnet for generating a B0 magnetic field within the imaging zone;
  a memory containing machine executable instructions, and pulse sequence commands;
  a processor for controlling the medical instrument, wherein execution of the machine executable instructions causes the processor to:
    acquire the magnetic resonance data by controlling the magnetic resonance imaging system with the pulse sequence commands;
    receive a subject magnetic susceptibility map of the subject;
    calculate a B0 inhomogeneity map from the magnetic resonance data;
    calculate a subject B0 magnetic field perturbation from the subject magnetic susceptibility map;
    calculate a residual B0 magnetic field perturbation by subtracting the subject B0 magnetic field perturbation from the B0 inhomogeneity map; and
    calculate a bone map from the residual B0 magnetic field perturbation.

2. The medical instrument of claim 1, wherein execution of the machine executable instructions further causes the processor to:
  reconstruct at least a portion of the magnetic resonance data into at least one subject magnetic resonance image;
  calculate a subject model by segmenting the subject magnetic resonance image; and
  construct the subject magnetic susceptibility map from the subject model.

3. The medical instrument of claim 2, wherein the pulse sequence commands comprise commands for acquiring the magnetic resonance imaging data according to a Dixon magnetic resonance imaging protocol, wherein the at least one subject magnetic resonance image comprises at least one fat image and at least one water image, and wherein the subject model comprises a fat portion and a water portion, and wherein the subject magnetic susceptibility map is calculated by adding a spatially dependent contribution to magnetic susceptibility from the fat portion and the water portion.

4. The medical instrument of claim 2, wherein execution of the instructions further causes the processor to calculate a spatial bone distribution by applying an inverted Green's function to the residual B0 magnetic field perturbation, wherein the bone map is at least partially calculated from the spatial bone distribution.

5. The medical instrument of claim 2, wherein execution of the instructions further causes the processor to:
  estimate a spatial bone distribution; and
  iteratively refine the spatial bone distribution by applying a Green's function to the spatial bone distribution to calculate an estimated B0 magnetic field perturbation and comparing the estimated B0 magnetic field perturbation to the the residual B0 magnetic field perturbation in an optimization algorithm, wherein the bone map is at least partially calculated from the spatial bone distribution.

6. The medical instrument of claim 4, wherein execution of the instructions further cause the processor to:
  calculate the bone map by segmenting the at least one subject magnetic resonance image; and
  adjust the bone map using the spatial bone distribution.

7. The medical instrument system of claim 6, wherein the calculation of the segmented bone image comprises weighting the segmentation using the spatial bone distribution.

8. The medical instrument of claim 2, wherein execution of the instructions further cause the processor to calculate a radiation attenuation map using the bone map and the subject model.

9. The medical instrument of claim 8, wherein the medical instrument further comprises a nuclear medical imaging system for acquiring a nuclear medical image of at least the imaging zone, wherein execution of the machine executable instructions further causes the processor to:
- acquire nuclear medical imaging data from the imaging zone; and
- reconstruct the nuclear medical image using the nuclear medical imaging data and the radiation attenuation map.

10. The medical instrument of claim 8, wherein execution of the machine executable instructions further cause the processor to:
- receive a treatment plan; and
- generate radiation therapy system control commands using the treatment plan and the radiation attenuation map.

11. The medical instrument of claim 10, wherein the medical instrument further comprises a radiation therapy system for irradiating a target within the imaging zone, wherein execution of the machine executable instructions further causes the processor to control the radiation therapy system with the radiation therapy system control commands.

12. The medical instrument of claim 1, wherein execution of the machine executable instructions further causes the processor to:
- receive a background B0 magnetic field map descriptive of the B0 magnetic field within the imaging zone; and
- correct the B0 inhomogeneity map with the background B0 magnetic field map before calculating the residual B0 magnetic field perturbation.

13. A method of operating an medical, wherein the medical instrument comprises a magnetic resonance imaging system for acquiring magnetic resonance data from a subject within an imaging zone, wherein the magnetic resonance imaging system comprises a main magnet for generating a B0 magnetic field within an imaging zone, wherein the method comprises the steps of:
- acquiring the magnetic resonance data by controlling the magnetic resonance imaging system with pulse sequence commands;
- receiving a subject magnetic susceptibility map of the subject;
- calculating a B0 inhomogeneity map from the magnetic resonance data;
- calculating a subject B0 magnetic field perturbation from the subject magnetic susceptibility map;
- calculating a residual B0 magnetic field perturbation by subtracting the subject B0 magnetic field perturbation from the B0 inhomogeneity map; and
- calculating a bone map from the residual B0 magnetic field perturbation.

14. A computer program product comprising machine executable instructions for execution by a processor controlling a medical instrument wherein the medical instrument comprises a magnetic resonance imaging system for acquiring magnetic resonance data from a subject within an imaging zone, wherein the magnetic resonance imaging system comprises a main magnet for generating a B0 magnetic field within an imaging zone, wherein execution of the machine executable instructions causes the processor to:
- acquire the magnetic resonance data by controlling the magnetic resonance imaging system with pulse sequence commands;
- receive a subject magnetic susceptibility map of the subject;
- calculate a B0 inhomogeneity map from the magnetic resonance data;
- calculate a subject B0 magnetic field perturbation from the subject magnetic susceptibility map;
- calculate a residual B0 magnetic field perturbation by subtracting the subject B0 magnetic field perturbation from the B0 inhomogeneity map; and
- calculate a bone map from the residual B0 magnetic field perturbation.

* * * * *